United States Patent [19]

Tetzner

[11] Patent Number: 5,077,294
[45] Date of Patent: Dec. 31, 1991

[54] PRODUCTS CONTAINING VERAPAMIL OR GALLOPAMIL AND PRAZOSIN

[75] Inventor: Christine Tetzner, Ludwigshafen, Fed. Rep. of Germany

[73] Assignee: BASF Aktiengesellschaft, Ludwigshafen, Fed. Rep. of Germany

[21] Appl. No.: 508,484

[22] Filed: Apr. 13, 1990

Related U.S. Application Data

[63] Continuation of Ser. No. 319,854, Mar. 6, 1989, abandoned, which is a continuation of Ser. No. 92,549, Sep. 3, 1987, abandoned.

[30] Foreign Application Priority Data

Jul. 25, 1987 [DE] Fed. Rep. of Germany ....... 3724644

[51] Int. Cl.$^5$ .................. A61K 31/50; A61K 31/275; A61K 31/495
[52] U.S. Cl. ..................................... 514/254; 514/523
[58] Field of Search ................................ 514/523, 254

[56] References Cited

PUBLICATIONS

Therapiewoche 34 (1984) 7009, Konig, et al.
British J. Clin. Pharmac. 21 (1986), 143 S., Muller et al.
Drug Research 20 (1970), 799.
Medwelt 35 (1984), 1534, Gabriel.
Munch. med. Wschr. 127 (1985), 379, Mauersberger.
Clin. Pharmacol. Ther. 36 (1984), 716 Pasanisi et al.
British M. Clin. Pharmac. 18 (1984), 290 P., Pasanisi et al.
Reinfrank et al., Abstracts Third European Meeting on Hypertension, Milan, Italy, (Jun. 14–17, 1987), pp. 463–464.
Reingrank et al., Second Annual Meeting of the American Society of Hypertension, New York, N.Y. (May 16–21, 1987) Abstracts, p. A282.
Grossmann et al., Sep. 1980, Mal. Cell. Edocrinol, 19(3):243–51, Abstract only.
Physican's Desk Reference 40th Ed. (1986) p. 981.
Journal of Cardiovascular Pharmacology, Supp. 10, pp. 5108–5110 (1987) Elliott, et al., "Verapamil and . . . Combination", In related application [Ser. No. 07/220,473].

*Primary Examiner*—Allen J. Robinson
*Attorney, Agent, or Firm*—Keil & Weinkauf

[57] ABSTRACT

Products contain verapamil or gallopamil and prazosin, in each case in depot form, as a combination preparation for simultaneous use in the therapy of high blood pressure.

5 Claims, No Drawings

PRODUCTS CONTAINING VERAPAMIL OR GALLOPAMIL AND PRAZOSIN

This application is a continuation of application Ser. No. 319,854, filed Mar. 6, 1989, now abandoned, which is a continuation of application Ser. No. 092,549, filed Sept. 3, 1987, now abandoned.

It is known that verapamil (5-[N-3,4-dimethoxyphenethyl-N-methylamino]-2-(3,4-dimethoxyphenyl)-2-isopropylvaleronitrile), gallopamil (5-[N-3,4-dimethoxyphenethyl-N-methylamino]-2-(3,4,5-trimethoxyphenyl)-2-isopropylvaleronitrile) and prazosin (4-amino-2-[4-(2-furoyl)-piperazin-1-yl]-6,7-dimethoxyquinazoline) have hypotensive properties (Therapiewoche 34 (1984) 7009, Brit. J. Clin. Pharmac. 21 (1986), 143 S, Drug Research 20 (1970), 799, medwelt 35 (1984), 1534 and Münch. med. Wschr. 127 (1985), 379).

It is also known that a combination of verapamil and prazosin has superadditive properties (Clin. Pharmacol. Ther. 36 (1984), 716, and Br. J. Clin. Pharmac. 18 (1984), 290 P). However, the simultaneous administration of both substances or of a combination of the two substances leads to an excessive fall in blood pressure which is accompanied by orthostatic symptoms which occur more frequently than with prazosin alone (Clin. Pharmacol. Ther. 36 (1984), 716 (left-hand column)).

We have found, surprisingly, that verapamil and gallopamil can be administered as a sustained release form together with prazosin.

The present invention relates to products containing verapamil or gallopamil and prazosin, in each case in sustained release form, as a combination preparation for simultaneous use in the therapy of high blood pressure.

The combination preparation contains the verapamil and prazosin in a ratio of from 400:1 to 50:1, preferably from 250:1 to 100:1, and the gallopamil and the prazosin in a ratio of from 200:1 to 25:1, preferably from 100:1 to 50:1.

Since the three substances contain basic groups, they can also be used, for the combination preparation, in the form of their salts with physiologically tolerated acids. Preferred physiologically tolerated acids are hydrochloric acid, sulfuric acid, phosphoric acid, acetic acid, citric acid, malonic acid, salicylic acid, maleic acid, fumaric acid, succinic acid, ascorbic acid, malic acid, methanesulfonic acid, lactic acid, gluconic acid, glucuronic acid, amidosulfonic acid, benzoic acid and tartaric acid.

The novel administration form is much better tolerated than the conventional combinations of verapamil and prazosin. For example, it has been found that the administration of 160 mg of verapamil plus 1 mg of prazosin gives rise to orthostatic symptoms in 6 out of 8 test subjects (Clin. Pharmacol. Ther. 36 (1984), 716; cf. in particular page 717, left-hand column, Paragraphs 3 and 4, and page 719, left-hand column, last complete paragraph). In contrast, no orthostatic symptoms were observed after the administration of 240 mg of verapamil plus 1, 2, 3 or 4 mg of prazosin in sustained release form to 46 patients.

The novel administration form is given orally. Tablets, coated tablets and capsules are particularly suitable for this purpose.

The daily dose is preferably about 240 mg of verapamil or 100 mg of gallopamil hydrochloride in combination with from 1 to 2 mg of prazosin.

The sustained release or retard forms can be prepared using the conventional methods (cf. H. Sucker et al.: Pharmazeutische Technologie, Thieme-Verlag, Stuttgart 1978). The Examples which follow illustrate preferred embodiments.

EXAMPLE 1

Tablets having the following composition are prepared in a conventional manner:

| | |
|---|---|
| verapamil hydrochloride | 240.0 mg |
| prazosin hydrochloride | 1.1 mg |
| sodium alginate | 339.9 mg |
| polyvinylpyrrolidone (molecular weight 20,000) | 25.0 mg |
| corn starch | 40.0 mg |
| magnesium stearate | 4.0 mg |
| | 510.0 mg |

With the exception of the magnesium stearate, the abovementioned substances are mixed, thoroughly moistened with water and granulated, and the granules are dried and sieved. The magnesium stearate is admixed and the mixture is then pressed to give tablets. The tablets are then coated with a hydroxypropyl-based film coating which is soluble in gastric juice.

EXAMPLE 2

The tablets obtained as described in Example 1 are provided with a tablet coating consisting of 5 parts of sucrose, 2 parts of corn starch, 2 parts of calcium carbonate and 1 part of talc.

EXAMPLE 3

Pellets having the following composition are prepared in a conventional manner:

| | |
|---|---|
| verapamil hydrochloride | 240.0 mg |
| prazosin hydrochloride | 2.0 mg |
| sugar pellets | 70.0 mg |
| silica | 2.0 mg |
| sodium dioctylsulfosuccinate | 2.0 mg |
| PVP (Kollidon ® 30) | 15.0 mg |
| microcrystalline cellulose | 20.0 mg |
| polyethylene glycol 6000 | 3.0 mg |
| polyethylene glycol 400 | 1.0 mg |
| Eudragit ® RS | 20.0 mg |
| talc | 5.0 mg |
| | 380.0 mg |

The sugar pellets are initially taken in a coating vessel. Thereafter, a solution of 5% strength PVP in water is sprayed onto the sugar pellets, and a powdered mixture of verapamil, prazosin and silica is applied. The resulting pellets are then dried. The process is repeated until the powdered mixture and about ⅓ of the PVP have been consumed. The remaining PVP, in the form of a 20% strength solution, is then applied, a little at a time, onto the pellets and sprayed with very finely milled microcrystalline cellulose. After each application step, the product is dried with warm air. The pellets thus produced are then film-coated with a solution of sodium dioctylsulfosuccinate, polyethylene glycol 6000 and 400 and Eudragit ® RS.

EXAMPLES 4 TO 6

Examples 1 to 3 are repeated, except that 100 mg of gallopamil hydrochloride are used instead of 240 mg of verapamil hydrochloride.

EXAMPLE 7

30 tablets of ISOPTIN ® RR and 30 tablets of MINI-PRESS ®-retard are introduced in pairs into a press-through pack.

I claim:

1. A pharmaceutical composition for the treatment of high blood pressure, said composition being in sustained release form for oral administration, which composition comprises: gallopamil in combination with prazosin, in a weight ratio of gallopamil to prazosin of from about 100:1.

2. The composition of claim 1 in tablet or capsule form.

3. A method of treating high blood pressure comprising simultaneously administering to an individual in need thereof an effective amount of sustained-released gallopamil and an effective amount of sustained-released prazosin, said gallopamil and said prazosin being orally administered in a weight ratio of gallopamil to prazosin of from about 100:1.

4. The method of claim 3, wherein said gallopamil is combined with said prazosin in single dosage form.

5. The method of claim 3, wherein said gallopamil is administered separate from, but concurrently with, said prazosin.

* * * * *